United States Patent [19]
Jeanmart et al.

[11] 3,948,917
[45] Apr. 6, 1976

[54] 1,4-DITHIINO[2,3-c]PYRROLE DERIVATIVES

[75] Inventors: Claude Jeanmart, Brunoy; Andre Leger, Paris; Mayer Naoum Messer, Bievres, all of France

[73] Assignee: Rhone-Poulenc S.A., Paris, France

[22] Filed: Dec. 3, 1973

[21] Appl. No.: 421,060

[30] Foreign Application Priority Data
Dec. 4, 1972 France .............................. 72.43054
Oct. 19, 1973 France .............................. 73.37402

[52] U.S. Cl. ..... 260/268 BQ; 260/268 BC; 424/250
[51] Int. Cl.² ...................................... C07D 409/14
[58] Field of Search .... 260/268 BC, 268 BQ, 268 C

[56] References Cited
UNITED STATES PATENTS
3,818,011  6/1974  Challier et al. ............... 260/268 BC
3,847,921  11/1974  Cotrel et al. .................. 260/268 BC

OTHER PUBLICATIONS
Zdzislaw Kleinrock et al. Chemical Abstracts Vol. 75, p. 196, (1971).

*Primary Examiner*—Richard J. Gallagher
*Assistant Examiner*—Jose Tovar
*Attorney, Agent, or Firm*—Stevens, Davis, Miller & Mosher

[57] ABSTRACT

New compounds of the formula:

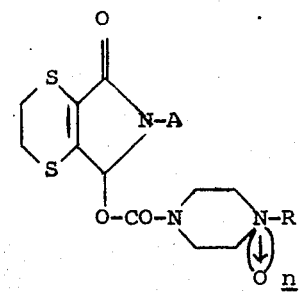

wherein A is a phenyl, pyridyl, pyridazinyl, 2-, 3- or 4-quinolyl or naphthyridinyl radical, or a said radical substituted by one or two atoms or radicals selected from halogen, alkyl, alkoxy cyano and nitro, R is alkyl, alkenyl or hydroxyalkyl, and $n$ is zero or 1, possess pharmacological properties and are, in particular, active as tranquilisers, anti-convulsant agents, decontracturants and agents to produce hypnosis.

8 Claims, No Drawings

1,4-DITHIINO(2,3-C)PYRROLE DERIVATIVES

This invention relates to new therapeutically useful 1,4-dithiino[2,3-c]pyrrole derivatives, processes for their preparation and pharmaceutical compositions containing them.

The new 1,4-dithiino[2,3-c]pyrrole derivatives of the present invention are those of the general formula:

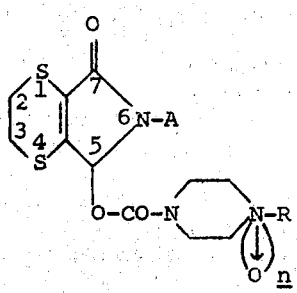    I wherein A represents a phenyl, pyridyl, pyridazinyl, 2-, 3- or 4-quinolyl or naphthyridinyl radical, each such radical being optionally substituted by one or two atoms or radicals, which — when two substituents are present — may be the same or different, selected from halogen atoms (preferably chlorine), alkyl radicals containing from 1 to 4 carbon atoms (preferably methyl), alkoxy radicals containing from 1 to 4 carbon atoms (preferably methoxy), and cyano and nitro radicals, R represents an alkyl radical containing from 1 to 4 carbon atoms (preferably methyl), an alkenyl radical containing from 2 to 4 carbon atoms (preferably allyl) or a hydroxyalkyl radical containing from 1 to 4 carbon atoms (preferably 2-hydroxyethyl), and n represents zero or 1, and acid addition salts thereof.

According to a feature of the invention, the compounds of general formula I, wherein A, R and n are as hereinbefore defined, are prepared by the process which comprises reacting a piperazine derivative of the general formula:

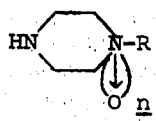    II (wherein R and n are as hereinbefore defined) with a mixed carbonate of the general formula:

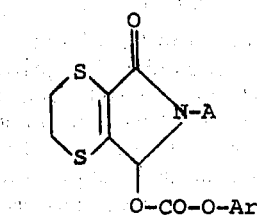    III wherein A is as hereinbefore defined and Ar represents a phenyl radical optionally substituted by an alkyl radical containing from 1 to 4 carbon atoms. The reaction is generally carried out in an inert organic solvent, for example acetonitrile, at a temperature between 0° and 50°C.

The mixed carbonates of general formula III can be obtained by reacting a chloroformate of the general formula:

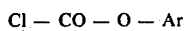    IV (wherein Ar is as hereinbefore defined) with a 1,4-dithiino[2,3-c]pyrrole derivative of the general formula:

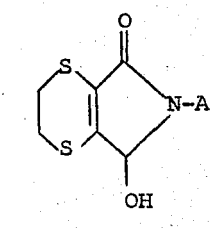    V wherein A is as hereinbefore defined. The reaction is generally carried out in an organic solvent, for example tetrahydrofuran, in the presence of an alkaline condensation agent or in a basic organic solvent, for example pyridine.

The 1,4-dithiino[2,3-c]pyrrole derivatives of general formula V can be obtained by partial reduction of an imide of the general formula:

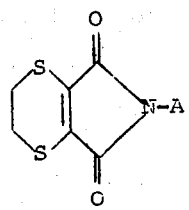    VI wherein A is as hereinbefore defined. The reduction is generally effected by means of an alkali metal borohydride in aqueous-organic or organic solution.

The imides of general formula VI can be obtained by reacting an amine of the general formula $H_2N$-A (wherein A is as hereinbefore defined) with 5,6-dihydro-1,4-dithiine-2,3-dicarboxylic acid anhydride. The reaction is generally carried out by heating the reactants in an organic solvent, for example ethanol or diphenyl ether.

5,6-Dihydro-1,4-dithiine-2,3-dicarboxylic acid anhydride can be prepared in accordance with the method described by H. R. Schweizer, Helv. Chim. Acta, 52, 2229 (1969).

According to another feature of the invention, the compounds of general formula I, wherein A and R are as hereinbefore defined and n is zero, are prepared by the process which comprises reacting a 1-chlorocarbonyl-piperazine of the general formula:

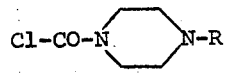    VII (wherein R is as hereinbefore defined) with an alkali metal salt, optionally prepared in situ, of a 1,4-dithiino[2,3-c]pyrrole derivative of general formula V. The reaction is generally carried out in an anhydrous organic solvent, for example benzene, toluene, tetrahydrofuran or dimethylformamide, at a temperature below 50° C.

The 1,4-dithiino[2,3-c]pyrrole derivatives of general formula I obtained by the aforementioned processes can be purified by physical methods such as distillation, crystallisation or chromatography, or by chemical methods such as the formation of salts, crystallisation of the salts and decomposition of them in an alkaline medium. In carrying out the said chemical methods the nature of the anion of the salt is immaterial, the only requirement being that the salt must be well-defined and readily crystallisable.

The 1,4-dithiino[2,3-c]pyrrole derivatives of general formula I may be converted by methods known per se into acid addition salts. The acid addition salts may be obtained by the action of acids on the new compounds in appropriate solvents. As organic solvents there may be used alcohols, ethers, ketones or chlorinated hydrocarbons. The salt which is formed is precipitated, if necessary after concentration of the solution, and is isolated by filtration or decantation.

By the term "methods known per se" as used in this specification is meant methods heretofore used or described in the chemical literature.

The 1,4-dithiino[2,3-c]pyrrole derivatives of the invention and their acid addition salts possess valuable pharmacological properties; they are particularly active as tranquillisers, anti-convulsant agents, decontracturants and agents to produce hypnosis. In animals (mice), they have proved active as such at doses of between 5 and 100 mg./kg. animal body weight when administered orally, in particular in the following tests:

i. electric battle according to a technique similar to that of Tedeschi et al. [J. Pharmacol., 125, 28 (1959)],
ii. pentetrazole-induced convulsion according to a technique similar to that of Everett and Richards [J. Pharmacol., 81, 402 (1944)], and
iii. supramaximal electric shock according to the technique of Swinyard et al. [J. Pharmacol, 106, 319 (1952)].

The $LD_{50}$ of the compounds of the invention when administered orally to mice is generally about, or greater than, 900 mg./kg. animal body weight.

Preferred 1,4-dithiino[2,3-c]pyrrole derivatives of the invention are those of general formula I wherein A represents a phenyl, 2-pyridyl, 3-pyridazinyl, 2-quinolyl or 1,8-naphthyridin-2-yl radical optionally substituted by a halogen (preferably chlorine) atom, an alkyl radical containing from 1 to 4 carbon atoms (preferably methyl), an alkoxy radical containing from 1 to 4 carbon atoms (preferably methoxy), or a cyano or nitro radical, R represents a methyl radical, and n is zero (as is preferred) or 1. Of outstanding importance are the 1,4-dithiino[2,3-c]pyrrole derivatives of general formula I obtained as products in Examples 18, 11, 1, 8 and 5 which follow.

For therapeutic purposes, the 1,4-dithiino[2,3-c]pyrrole derivatives of general formula I may be employed as such or in the form of non-toxic acid addition salts, i.e. salts containing anions which are relatively innocuous to the animal organism in therapeutic doses of the salts (such as hydrochlorides, sulphates, nitrates, phosphates, acetates, propionates, succinates, benzoates, fumarates, maleates, tartrates, theophyllinacetates, salicylates, phenolphthalinates and methylene-bis-β-hydroxynaphthoates) so that the beneficial physiological properties inherent in the bases are not vitiated by side effects ascribable to the anions.

The following Examples illustrate the invention.

EXAMPLE 1

A solution of 6-(5-chloropyrid-2-yl)-5-hydroxy-7-oxo-2,3,6,7-tetrahydro-1,4-dithiino[2,3-c]pyrrole (15.0 g.) in anhydrous tetrahydrofuran (150 cc.) is treated for 15 minutes at about 10°–15° C with sodium hydride (1.44 g.), and a solution of 1-chlorocarbonyl-4-methylpiperazine (24.4 g.) in anhydrous tetrahydrofuran (200 cc.) is then added, at 5° C. The reaction mixture is stirred for 4 hours at 5° C. After evaporating the solvent under reduced pressure (20 mm.Hg), the residue is dissolved in diethyl ether (450 cc.). The ether solution is rapidly extracted twice with an ice-cold normal aqueous solution of methanesulphonic acid (total 500 cc.). The combined aqueous extracts are rendered alkaline by adding 10N sodium hydroxide solution (100 cc.). The oil which separates out is extracted with methylene chloride (250 cc.) and then with diethyl ether (300 cc.). The combined organic extracts are washed five times with distilled water (total 250 cc.), dried over anhydrous sodium sulphate, treated with decolourising charcoal (0.1 g.) and evaporated. The crystals obtained (18.0 g.; m.p. 170° C.) are dissolved in boiling ethanol (225 cc.). After filtering the boiling solution and then cooling it for 3 hours at 2° C., the crystals which have appeared are filtered off, washed three times with ice-cold ethanol (total 45 cc.) and dried under reduced pressure (20 mm.Hg). 6-(5-chloropyrid-2-yl)-5-(4-methylpiperazin-1-yl)carbonyloxy-7-oxo-2,3,6,7-tetrahydro-1,4-dithiino[2,3-c]pyrrole (15.6 g.), melting at 180° C., is thus obtained.

6-(5-Chloropyrid-2-yl)-5-hydroxy-7-oxo-2,3,6,7-tetrahydro-1,4-dithiino[2,3-c]pyrrole employed as starting material can be obtained in the following way:

Preparation of 5,6-dihydro-1,4-dithiine-2,3-dicarboxylic acid anhydride, m.p. 113° C, according to H. R. Schweizer, Helv. Chim. Acta, 52, 2229 (1969).

Preparation of 6-(5-chloropyrid-2-yl)-5,7-dioxo-2,3,6,7-tetrahydro-1,4-dithiino[2,3-c]pyrrole (51.0 g.), m.p. 205° C, by reacting 2-amino-5-chloropyridine (24.0 g.) with 5,6-dihydro-1,4-dithiine-2,3-dicarboxylic acid anhydride (35.1 g.) in diphenyl ether, at 200° C, in the presence of anhydrous acetic acid (1 cc.).

Preparation of 6-(5-chloropyrid-2-yl)-5-hydroxy-7-oxo-2,3,6,7-tetrahydro-1,4-dithiino[2,3-c]pyrrole (49.8 g.), m.p. 200° C, by reacting potassium borohydride (6.9 g.) with 6-(5-chloropyrid-2-yl)-5,7-dioxo-2,3,6,7-tetrahydro-1,4-dithiino[2,3-c]pyrrole (51.0 g.), in anhydrous methanol at a temperature of about 20° C.

EXAMPLE 2

A solution of 5-hydroxy-7-oxo-6-(pyrid-2-yl)-2,3,6,7-tetrahydro-1,4-dithiino[2,3-c]pyrrole (6.0 g.) in anhydrous tetrahydrofuran (60 cc.) is treated for 17 minutes at about 5°–10° C, with sodium hydride (0.64 g.), and a solution of 1-chlorocarbonyl-4-methylpiperazine (11.0 g.) in anhydrous tetrahydrofuran (80 cc.) is then added, at 5° C. The reaction mixture is stirred for 4 hours at 5° C. After evaporating the solvent under reduced pressure (20 mm.Hg), the residue is dissolved in diethyl ether (300 cc.). The diethyl ether solution is washed three times with N sodium hydroxide solution (total 450 cc.) and then three times with distilled water (total 300 cc.), treated with vegetable charcoal (0.1 g.), dried over anhydrous potassium carbonate, filtered and evaporated. The residue (7.6 g.; m.p. 145° C.) is dissolved in boiling ethanol (20 cc.). After being cooled for 2 hours at 2° C, the crystals which have appeared are filtered off, washed twice with ice-cold ethanol (total 12 cc.) and dried under reduced pressure (20 mm.Hg). 5-(4-Methylpiperazin-1-yl)carbonyloxy-7-oxo-6-(pyrid-2-yl)-2,3,6,7-tetrahydro-1,4-dithiino[2,3-c]pyrrole (3.9 g.), melting at 150° C, is thus obtained.

5-Hydroxy-7-oxo-6-(pyrid-2-yl)-2,3,6,7-tetrahydro-1,4-dithiino[2,3-c]pyrrole employed as starting material can be prepared in the following way:
Preparation of 5,7-dioxo-6-(pyrid-2-yl)-2,3,6,7-tetrahydro-1,4-dithiino[2,3-c]pyrrole (92.0 g.), m.p. 210° C, by reacting 2-aminopyridine (37.6 g.) with 5,6-dihydro-1,4-dithiine-2,3-dicarboxylic acid anhydride (75.0 g.) in diphenyl ether, at 200° C, in the presence of anhydrous acetic acid (0.7 cc.).
Preparation of 5-hydroxy-7-oxo-6-(pyrid-2-yl)-2,3,6,7-tetrahydro-1,4-dithiino[2,3-c]pyrrole (67.0 g.), m.p. 160° C, by reacting potassium borohydride (14.3 g.) with 5,7-dioxo-6-(pyrid-2-yl)-2,3,6,7-tetrahydro-1,4-dithiino[2,3-c]pyrrole (92.0 g.) in anhydrous methanol at a temperature of about 20° C.

EXAMPLE 3

A solution of 5-hydroxy-6-(6-methoxypyridazin-3-yl)-7-oxo-2,3,6,7-tetrahydro-1,4-dithiino[2,3-c]pyrrole (8.9 g.) in anhydrous tetrahydrofuran (90 cc.) is treated for 30 minutes at about 15°–20° C, with sodium hydride (0.87 g.), and a solution of 1-chlorocarbonyl-4-methylpiperazine (19.5 g.) in anhydrous tetrahydrofuran (120 cc.) is then added, at 5° C. The reaction mixture is stirred for 4 hours at 5° C. After evaporating the solvent under reduced pressure (20 mm.Hg), the residue is taken up in an ice-cold normal aqueous solution of methanesulphonic acid (150 cc.). The acid solution obtained is rapidly washed twice with diethyl ether (total 100 cc.) and then rendered alkaline by adding 10N sodium hydroxide solution (25 cc.). The oil which separates out is extracted three times with methylene chloride (total 300 cc.). The combined organic extracts are washed twice with distilled water (total 100 cc.), dried over anhydrous magnesium sulphate and evaporated. The crystals obtained (8.7 g.; m.p. 196°–198° C.) are dissolved in boiling ethanol (300 cc.). After filtering the boiling solution and then cooling it for 3 hours at 2° C, the crystals which have appeared are filtered off, washed three times with ice-cold ethanol (total 45 cc.) and dried under reduced pressure (20 mm.Hg.). 6-(6-Methoxypyridazin-3-yl)-5-(4-methylpiperazin-1-yl)carbonyloxy-7-oxo-2,3,6,7-tetrahydro-1,4-dithiino[2,3-c]pyrrole (7.7 g.), melting at 200° C, is thus obtained.

5-Hydroxy-6-(6-methoxypyridazin-3-yl)-7-oxo-2,3,6,7-tetrahydro-1,4-dithiino[2,3-c]pyrrole employed as starting material can be prepared in the following way: Preparation of 5,7-dioxo-6-(6-methoxypyridazin-3-yl)-2,3,6,7-tetrahydro-1,4-dithiino[2,3-c]pyrrole (16.0 g.), m.p. 173° C, by reacting 3-amino-6-methoxypyridazine (12.5 g.) with 5,6-dihydro-1,4-dithiine-2,3-dicarboxylic acid anhydride (18.8 g.) in diphenyl ether at 200° C, in the presence of anhydrous acetic acid (0.5 cc.). Preparation of 5-hydroxy-6-(6-methoxypyridazin-3-yl)-7-oxo-2,3,6,7-tetrahydro-1,4-dithiino[2,3-c]pyrrole (12.1 g.), m.p. 206°–208° C, by reacting potassium borohydride (2.25 g.) with 5,7-dioxo-6-(6-methoxypyridazin-3-yl)-2,3,6,7-tetrahydro-1,4-dithiino[2,3-c]pyrrole (16.0 g.) in anhydrous methanol at a temperature of about 20° C.

EXAMPLE 4

A suspension of 5-hydroxy-7-oxo-6-phenyl-2,3,6,7-tetrahydro-1,4-dithiino[2,3-c]pyrrole (18.5 g.) in anhydrous toluene (100 cc.) is treated for 10 minutes at 20°–30° C, with a 2.2N solution of sodium methoxide in methanol (35 cc.). The solution obtained is evaporated at a temperature below or equal to 30° C. under reduced pressure (20 mm.Hg). The residue is dissolved in anhydrous toluene (200 cc.) and treated for 5 hours at 5° C, with a solution of 1-chlorocarbonyl-4-methylpiperazine (28.5 g.) in anhydrous toluene (100 cc.). The toluene solution is washed with N sodium hydroxide solution (200 cc.) and distilled water (100 cc.), dried over potassium carbonate and evaporated at a temperature below or equal to 50° C, under reduced pressure (20 mm.Hg). The oily residue obtained (30.0 g.) is treated with diisopropyl ether (180 cc.). After decanting the solvent, the residual gum is dissolved in boiling ethanol (60 cc.). After cooling for two hours at 2° C, the crystals which have appeared are filtered off, washed twice with ice-cold ethanol (total 10 cc.) and dried under reduced pressure (20 mm.Hg). 5-(4-Methylpiperazin-1-yl)carbonyloxy-7-oxo-6-phenyl-2,3,6,7-tetrahydro-1,4-dithiino[2,3-c]pyrrole (6.2 g.), melting at 140°–142° C, is thus obtained.

5-Hydroxy-7-oxo-6-phenyl-2,3,6,7-tetrahydro-1,4-dithiino[2,3,-c]pyrrole employed as starting material can be obtained in the following way:
Preparation of 5,7-dioxo-6-phenyl-2,3,6,7-tetrahydro-1,4-dithiino[2,3-c]pyrrole, m.p. 184° C. according to H. R. Schweizer, Helv. Chim. Acta, 52, 2233 (1969). Preparation of 5-hydroxy-7-oxo-6-phenyl-2,3,6,7-tetrahydro-1,4-dithiino[2,3-c]pyrrole (94.2 g.), m.p. 166° C, by reacting potassium borohydride (15.0 g.) with 5,7-dioxo-6-phenyl-2,3,6,7-tetrahydro-1,4-dithiino[2,3-c]pyrrole (97.7 g.) in anhydrous methanol at a temperature of about 20° C.

EXAMPLE 5

Following the procedure of Example 2 but starting with 5-hydroxy-6-(5-methylpyrid-2-yl)-7-oxo-2,3,6,7-tetrahydro-1,4-dithiino[2,3-c]pyrrole (14.0 g.), sodium hydride (1.45 g.) and 1-chlorocarbonyl-4-methylpiperazine (16.25 g.) in anhydrous tetrahydrofuran (250 cc.) and stirring the reaction mixture for 6 hours at 5° C, 5-(4-methylpiperazin-1-yl)-carbonyloxy-6-(5-methylpyrid-2-yl)-7-oxo-2,3,6,7-tetrahydro-1,4-dithiino[2,3-c]pyrrole (13.1 g.), melting at 169°–170° C. after recrystallisation from ethanol, is obtained.

5-Hydroxy-6-(5-methylpyrid-2-yl)-7-oxo-2,3,6,7-tetrahydro-1,4-dithiino[2,3-c]pyrrole employed as starting material can be obtained in the following way:
Preparation of 5,7-dioxo-6-(5-methylpyrid-2-yl)-2,3,6,7-tetrahydro-1,4-dithiino[2,3-c]pyrrole (41.3 g.), m.p. 250° C, by reacting 2-amino-5-methylpyridine (21.6 g.) with 5,6-dihydro-1,4-dithiine-2,3-dicarboxylic acid anhydride (37.6 g.) in diphenyl ether (100 cc.) at 200° C, for 2 hours in the presence of anhydrous acetic acid (0.5 cc.).
Preparation of 5-hydroxy-6-(5-methylpyrid-2-yl)-7-oxo-2,3,6,7-tetrahydro-1,4-dithiino[2,3-c]pyrrole (23.5 g.), m.p. 198°–200° C, by reacting potassium borohydride (4.3 g.) with 5,7-dioxo-6-(5-methylpyrid-2-yl)-2,3,6,7-tetrahydro-1,4-dithiino[2,3-c]pyrrole (27.8 g.) in anhydrous methanol (350 cc.) at a temperature of about 25° C.

EXAMPLE 6

Following the procedure of Example 1 but starting with 5-hydroxy-6-(5-nitropyrid-2-yl)-7-oxo-2,3,6,7-tetrahydro-1,4-dithiino[2,3-c]pyrrole (20.2 g.), sodium hydride (1.85 g.) and 1-chlorocarbonyl-4-methylpiperazine (21.2 g.) in anhydrous tetrahydrofuran (300 cc.) and stirring the reaction mixture for 4 hours at 5° C, 5-(4-methylpiperazin-1-yl)carbonyloxy-6-(5-nitropyrid-2-yl)-7-oxo-2,3,6,7-tetrahydro-1,4-dithiino[2,3-c]pyrrole (11.0 g.), melting at 245° C, after recrystallisation from a mixture of dimethylformamide and ethanol (1-1 by volume), is obtained.

5-Hydroxy-6-(5-nitropyrid-2-yl)-7-oxo-2,3,6,7-tetrahydro-1,4-dithiino[2,3-c]pyrrole employed as starting material can be obtained in the following way:
Preparation of 2-amino-5-nitropyridine, m.p. 186°–188° C, according to W. T. Caldwell and E. C. Kornfeld, J. Amer. Chem. Soc., 64, 1695 (1942).
Preparation of 5,7-dioxo-6-(5-nitropyrid-2-yl)-2,3,6,7-tetrahydro-1,4-dithiino[2,3-c]pyrrole (10.9 g.), m.p. 288° C, by reacting 2-amino-5-nitropyridine (13.9 g.) with 5,6-dihydro-1,4-dithiine-2,3-dicarboxylic acid anhydride (18.8 g.) in diphenyl ether (50 cc.) at 190° C, for half an hour in the presence of anhydrous acetic acid (0.4 cc.).
Preparation of 5-hydroxy-6-(5-nitropyrid-2-yl)-7-oxo-2,3,6,7-tetrahydro-1,4-dithiino[2,3-c]pyrrole (28.4 g.), m.p. 280° C, by reacting potassium borohydride (18.6 g.) with 5,7-dioxo-6-(5-nitropyrid-2-yl)-2,3,6,7-tetrahydro-1,4-dithiino[2,3-c]pyrrole (36.0 g.) in anhydrous methanol (1,000 cc.) at a temperature of about 25°–30° C.

EXAMPLE 7

Following the procedure of Example 2 but starting with 6-(5-cyanopyrid-2-yl)-5-hydroxy-7-oxo-2,3,6,7-tetrahydro-1,4-dithiino[2,3-c]pyrrole (14.6 g.), sodium hydride (1.45 g.) and 1-chlorocarbonyl-4-methylpiperazine (16.25 g.) in anhydrous tetrahydrofuran (250 cc.) and stirring the reaction mixture for 6 hours at 5° C, 6-(5-cyanopyrid-2-yl)-5-(4-methylpiperazin-1-yl)carbonyloxy-7-oxo-2,3,6,7-tetrahydro-1,4-dithiino[2,3-c]pyrrole (6.7 g.), melting at 220° C, after recrystallisation from acetonitrile, is obtained.

6-(5-Cyanopyrid-2-yl)-5-hydroxy-7-oxo-2,3,6,7-tetrahydro-1,4-dithiino[2,3-c]pyrrole employed as starting material can be obtained in the following way:
Preparation of 2-amino-5-cyanopyridine, m.p. 164° C, according to P. Z. Gregory et al, J. Chem. Soc., (1947), 87. Preparation of 6-(5-cyanopyrid-2-yl)-5,7-dioxo-2,3,6,7-tetrahydro-1,4-dithiino[2,3-c]pyrrole (49.6 g.), m.p. 278° C, by reacting 2-amino-5-cyanopyridine (32.0 g.) with 5,6-dihydro-1,4-dithiine-2,3-dicarboxylic acid anhydride (50.5 g.) in diphenyl ether (150 cc.) at 200° C, for 2 hours in the presence of anhydrous acetic acid (0.5 cc.). Preparation of 6-(5-cyanopyrid-2-yl)-5-hydroxy-7-oxo-2,3,6,7-tetrahydro-1,4-dithiino[2,3-c]pyrrole (35.0 g.), m.p. 236° C, by reacting potassium borohydride (6.6 g.) with 6-(5-cyanopyrid-2-yl)-5,7-dioxo-2,3,6,7-tetrahydro-1,4-dithiino[2,3-c]pyrrole (43.5 g.) in anhydrous methanol (450 cc.) at a temperature of about 25° C.

EXAMPLE 8

Following the procedure of Example 1 but starting with 5-hydroxy-6-(3-nitrophenyl)-7-oxo-2,3,6,7-tetrahydro-1,4-dithiino[2,3-c]pyrrole (15.5 g.), sodium hydride (1.45 g.) and 1-chlorocarbonyl-4-methylpiperazine (24.3 g.) in anhydrous tetrahydrofuran (250 cc.) and stirring the reaction mixture for 3 hours at 5° C, 5-(4-methylpiperazin-1-yl)carbonyloxy-6-(3-nitrophenyl)-7-oxo-2,3,6,7-tetrahydro-1,4-dithiino[2,3-c]pyrrole (12.9 g.), melting at 180° C. after recrystallisation from ethyl acetate, is obtained.

5-Hydroxy-6-(3-nitrophenyl)-7-oxo-2,3,6,7-tetrahydro-1,4-dithiino[2,3-c]pyrrole employed as starting material can be obtained in the following way:
Preparation of 6-(3-nitrophenyl)-5,7-dioxo-2,3,6,7-tetrahydro-1,4-dithiino[2,3-c]pyrrole, m.p. 214° C, according to H. R. Schweizer, Helv. Chim. Acta, 52, 2233 (1969).
Preparation of 5-hydroxy-6-(3-nitrophenyl)-7-oxo-2,3,6,7-tetrahydro-1,4-dithiino[2,3-c]pyrrole (55.5 g.), m.p. 220° C, by reacting potassium borohydride (11.0 g.) with 6-(3-nitrophenyl)-5,7-dioxo-2,3,6,7-tetrahydro-1,4-dithiino[2,3-c]pyrrole (68.0 g.) in anhydrous methanol (800 cc.) at a temperature of about 25° C.

EXAMPLE 9

Following the procedure of Example 1 but starting with 6-(3-chlorophenyl)-5-hydroxy-7-oxo-2,3,6,7-tetrahydro-1,4-dithiino[2,3-c]pyrrole (15.0 g.), sodium hydride (1.32 g.) and 1-chlorocarbonyl-4-methylpiperazine (12.5 g.) in anhydrous tetrahydrofuran (200 cc.) and stirring the reaction mixture for 1½ hours at 5° C, 6-(3-chlorophenyl)-5-(4-methylpiperazin-1-yl)carbonyloxy-7-oxo-2,3,6,7-tetrahydro-1,4-dithiino[2,3-c]pyrrole (8.9 g.), melting at 140° C. after recrystallisation from a mixture of ethyl acetate and diisopropyl ether (1-1 by volume), is obtained.

6-(3-Chlorophenyl)-5-hydroxy-7-oxo-2,3,6,7-tetrahydro-1,4-dithiino[2,3-c]pyrrole employed as starting material can be obtained in the following way:
Preparation of 6-(3-chlorophenyl)-5,7-dioxo-2,3,6,7-tetrahydro-1,4-dithiino[2,3-c]pyrrole (39.1 g.), m.p. 160° C, by reacting 3-chloroaniline (19.7 g.) with 5,6-dihydro-1,4-dithiine-2,3-dicarboxylic acid anhydride (28.2 g.) in refluxing anhydrous ethanol (225 cc.) for 6 hours in the presence of anhydrous acetic acid (0.45 cc.). Preparation of 6-(3-chlorophenyl)-5-hydroxy-7-oxo-2,3,6,7-tetrahydro-1,4-dithiino[2,3-c]pyrrole (23.0 g.), m.p. 172° C, by reacting potassium borohydride (3.6 g.) with 6-(3-chlorophenyl)-5,7-dioxo-2,3,6,7-tetrahydro-1,4-dithiino[2,3-c]pyrrole (26.0 g.) in anhydrous methanol (250 cc.) at a temperature of about 25° C.

EXAMPLE 10

Following the procedure of Example 1 but starting with 6-(4-chlorophenyl)-5-hydroxy-7-oxo-2,3,6,7-tetrahydro-1,4-dithiino[2,3-c]pyrrole (18.0 g.), sodium hydride (1.6 g.) and 1-chlorocarbonyl-4-methylpiperazine (15.0 g.) in anhydrous tetrahydrofuran (240 cc.) and stirring the reaction mixture for half an hour at 5° C, 6-(4-chlorophenyl)-5-(4-methylpiperazin-1-yl)carbonyloxy-7-oxo-2,3,6,7-tetrahydro-1,4-dithiino[2,3-c]pyrrole (17.1 g.), melting at 178° C. after recrystallisation from acetonitrile, is obtained.

6-(4-Chlorophenyl)-5-hydroxy-7-oxo-2,3,6,7-tetrahydro-1,4-dithiino[2,3-c]pyrrole employed as starting material can be obtained in the following way:
Preparation of 6-(4-chlorophenyl)-5,7-dioxo-2,3,6,7-tetrahydro-1,4-dithiino[2,3-c]pyrrole, m.p. 180° C, according to H. R. Schweizer, Helv. Chim. Acta, 52, 2233 (1969).
Preparation of 6-(4-chlorophenyl)-5-hydroxy-7-oxo-2,3,6,7-tetrahydro-1,4-dithiino[2,3-c]pyrrole (24.5 g.), m.p. 198° C, by reacting potassium borohydride (4.0 g.) with 6-(4-chlorophenyl)-5,7-dioxo-2,3,6,7-tetrahydro-1,4-dithiino[2,3-c]pyrrole (30.0 g.) in anhydrous methanol (300 cc.) at a temperature of about 25° C.

EXAMPLE 11

6-(7-Chloroquinol-2-yl)-5-hydroxy-7-oxo-2,3,6,7-tetrahydro-1,4-dithiino[2,3-c]pyrrole (9.0 g.) is added over the course of half an hour, at 15°–20° C, to a suspension of sodium hydride (1.35 g.) in anhydrous tetrahydrofuran (250 cc.). The reaction mixture is diluted with anhydrous dimethylformamide (50 cc.). 6-(7-Chloroquinol-2-yl)-5-hydroxy-7-oxo-2,3,6,7-tetrahydro-1,4-dithiino[2,3-c]pyrrole (a further 9.0 g.) is added over the course of half an hour, at 15° C, and then 1-chlorocarbonyl-4-methylpiperazine (25.0 g.) dissolved in anhydrous tetrahydrofuran (150 cc.) is added at 5° C. The reaction mixture is stirred for 4 hours at 5° C. After evaporating the tetrahydrofuran under reduced pressure (20 mm. Hg), the reaction mixture is treated with water (500 cc.). The gummy precipitate which has appeared is filtered off and taken up in an ice-cold 2N aqueous solution of methanesulphonic acid (350 cc.). The ice-cold aqueous acid solution is filtered and then rendered alkaline by adding 10N sodium hydroxide solution. The oil which separates out is extracted three times with methylene chloride (total 600 cc.). The organic solution is washed three times with distilled water (total 450 cc.), dried over anhydrous sodium sulphate, treated with decolourising charcoal (1.0 g.) and evaporated. The partially crystalline residue obtained (13.3 g.) is dissolved in boiling acetonitrile (170 cc.). After cooling for 2 hours at 2° C, the crystals which have appeared are filtered off, washed twice with ice-cold acetonitrile (total 40 cc.) and dried under reduced pressure (20 mm. Hg). 6-(7-Chloroquinol-2-yl)-5-(4-methylpiperazin-1-yl)carbonyloxy-7-oxo-2,3,6,7-tetrahydro-1,4-dithiino[2,3-c]pyrrole (6.9 g.), melting at 192° C, is thus obtained.

6-(7-Chloroquinol-2-yl)-5-hydroxy-7-oxo-2,3,6,7-tetrahydro-1,4-dithiino[2,3-c]pyrrole employed as starting material can be obtained in the following way:
Preparation of 2,7-dichloroquinoline according to R. E. Lutz et al., J. Amer. Chem. Soc., 68, 1322 (1946).
Preparation of 2-amino-7-chloroquinoline (10 g.), m.p. 175° C, by heating a mixture of 2,7-dichloroquinoline (36.7 g.) and 16N ammonia (700 cc.) in an autoclave at 125° C. for 25 hours.
Preparation of 6-(7-chloroquinol-2-yl)-5,7-dioxo-2,3,6,7-tetrahydro-1,4-dithiino[2,3-c]pyrrole (5.6 g.), m.p. 250° C, by reacting 2-amino-7-chloroquinoline (3.6 g.) with 5,6-dihydro-1,4-dithiine-2,3-dicarboxylic acid anhydride (3.8 g.) in diphenyl ether (10 cc.) at 200° C, for 45 minutes in the presence of anhydrous acetic acid (0.05 cc.).
Preparation of 6-(7-chloroquinol-2-yl)-5-hydroxy-7-oxo-2,3,6,7-tetrahydro-1,4-dithiino[2,3-c]pyrrole (5.3 g.), m.p. 222° C, by reacting potassium borohydride (0.65 g.) with 6-(7-chloroquinol-2-yl)-5,7-dioxo-2,3,6,7-tetrahydro-1,4-dithiino[2,3-c]pyrrole (5.6 g.) in anhydrous methanol (60 cc.) at a temperature of about 25° C.

EXAMPLE 12

A suspension of sodium hydride (1.11 g.) in anhydrous tetrahydrofuran (120 cc.) is treated for 20 minutes at about 10°–15° C. with 6-(5-chloropyrid-2-yl)-5-hydroxy-7-oxo-2,3,6,7-tetrahydro-1,4-dithiino[2,3-c]pyrrole (11.6 g.), and a solution of 1-chlorocarbonyl-4-ethylpiperazine (20.4 g.) in anhydrous tetrahydrofuran (160 cc.) is then added, at 5° C. The reaction mixture is stirred for 4 hours at 5° C. After evaporating the solvent under reduced pressure (20 mm. Hg), the residue is dissolved in diethyl ether (400 cc.). The ether solution is washed twice with ice-cold normal sodium hydroxide solution (total 300 cc.) and three times with distilled water (total 300 cc.), treated with decolourising charcoal (0.2 g.), dried over anhydrous sodium sulphate, filtered and evaporated. The residue (13.8 g.; m.p. 140° C.) is dissolved in boiling ethanol (25 cc.). After cooling for 3 hours at 2° C, the crystals which have appeared are filtered off, washed twice with ice-cold ethanol (total 20 cc.) and dried under reduced pressure (20 mm. Hg). 6-(5-Chloropyrid-2-yl)-5-(4-ethylpiperazin-1-yl)carbonyloxy-7-oxo-2,3,6,7-tetrahydro-1,4-dithiino[2,3-c]pyrrole (4.9 g.), melting at 163° C, is thus obtained.

6-(5-Chloropyrid-2-yl)-5-hydroxy-7-oxo-2,3,6,7-tetrahydro-1,4-dithiino[2,3-c]pyrrole employed as starting material is prepared as described in Example 1.

1-Chlorocarbonyl-4-ethylpiperazine can be prepared by reacting phosgene (58.4 g.) with 1-ethylpiperazine (40.0 g.) in toluene (700 cc.) at a temperature between 0° and 5° C. After isolating the dihydrochloride, m.p. 240° C, the base is liberated by the usual means and distilled. 1-Chlorocarbonyl-4-ethylpiperazine (25.7 g.), b.p. 87° C./0.2 mm. Hg, is obtained.

EXAMPLE 13

6-(5-Chloropyrid-2-yl)-7-oxo-5-phenoxycarbonyloxy-2,3,6,7-tetrahydro-1,4-dithiino[2,3-c]pyrrole (10.0 g.) and 1-isopropylpiperazine (6.1 g.) in anhydrous acetonitrile (100 cc.) is stirred for 20 hours at a temperature of about 25° C. The reaction mixture is filtered and then evaporated under reduced pressure (20 mm. Hg). The residue is dissolved in methylene chloride (250 cc.). The organic solution is washed twice with N sodium hydroxide solution (total 160 cc.) and once with distilled water (80 cc.) and then evaporated. The residue is dissolved in an ice-cold 0.5N aqueous solution of methanesulphonic acid (200 cc.). The aqueous acid solution is washed twice with diethyl ether (total 100 cc.) and then rendered alkaline by adding 10N sodium hydroxide solution. The oil which separates out is extracted twice with methylene chloride (total 240 cc.). The organic solution is washed three times with distilled water (total 240 cc.) dried over anhydrous sodium sulphate, treated with decolourising charcoal (0.2 g.) and evaporated. The crystals obtained (10.3 g.; m.p. 130°–135° C.) are dissolved in boiling acetonitrile (26 cc.). After filtering the boiling solution and then cooling it for 2 hours at 2° C, the crystals which have appeared are filtered off, washed twice with ice-cold acetonitrile (total 15 cc.) and dried under reduced pressure (20 mm. Hg). 6-(5-Chloropyrid-2-yl)-5-(4-isopropylpiperazin-1-yl)carbonyloxy-7-oxo-2,3,6,7-tetrahydro-1,4-dithiino[2,3-c]pyrrole (6.9 g.), melting at 156° C, is thus obtained.

6-(5-Chloropyrid-2-yl)-7-oxo-5-phenoxycarbonyloxy-2,3,6,7-tetrahydro-1,4-dithiino[2,3-c]pyrrole employed as starting material can be prepared by reacting sodium hydride (3.4 g.) and then phenyl chloroformate (20.4 cc.) with 6-(5-chloropyrid-2-yl)-5-hydroxy-7-oxo-2,3,6,7-tetrahydro-1,4-dithiino[2,3-c]pyrrole (34.8 g.) in anhydrous tetrahydrofuran (560 cc.) for 4 hours at 5° C. After evaporating the solvent, dissolving the residue in methylene chloride, washing the solution with alkali, evaporating the solvent and then recrystallising the crystals obtained (41.5 g.) from toluene (185 cc.), 6-(5-chloropyrid-2-yl)-7-oxo-5-phenoxycarbonyloxy-2,3,6,7-tetrahydro-1,4-dithiino[2,3-c]pyrrole (34.2 g.), which melts at 178° C, is obtained.

EXAMPLE 14

Following the procedure of Example 13 but starting with 6-(5-chloropyrid-2-yl)-7-oxo-5-phenoxycarbonyloxy-2,3,6,7-tetrahydro-1,4-dithiino[2,3-c]pyrrole (10.0 g.) and 1-allylpiperazine (6.0 g.) in anhydrous acetonitrile (100 cc.) and stirring the reaction mixture for 48 hours at a temperature of about 25° C, 5-(4-allylpiperazin-1-yl)carbonyloxy-6-(5-chloropyrid-2-yl)-7-oxo-2,3,6,7-tetrahydro-1,4-dithiino[2,3c]pyrrole (7.9 g.), melting at 130° C. after recrystallisation from ethanol, is obtained.

EXAMPLE 15

Following the procedure of Example 13 but starting with 6-(5-chloropyrid-2-yl)-7-oxo-5-phenoxycarbonyloxy-2,3,6,7-tetrahydro-1,4-dithiino[2,3-c]pyrrole (13.7 g.) and 1-(2-hydroxyethyl)piperazine (8.5 g.) in anhydrous acetonitrile (140 cc.) and stirring the reaction mixture for 24 hours at a temperature of about 25° C, 6-(5-chloropyrid-2-yl)-5-[4-(2-hydroxyethyl)-piperazin-1-yl]carbonyloxy-7-oxo-2,3,6,7-tetrahydro-1,4-dithiino[2,3-c]pyrrole (8.2 g.), melting at 154° C. after recrystallisation from acetonitrile, is obtained.

EXAMPLE 16

5-Hydroxy-6-(1,8-naphthyridin-2-yl)-7-oxo-2,3,6,7-tetrahydro-1,4-dithiino[2,3-c]pyrrole (8.45 g.) is added, at 0° C, to a suspension of sodium hydride (0.8 g.) in anhydrous dimethylformamide (125 cc.). The reaction mixture is stirred for half an hour at 0° C, and 1-chlorocarbonyl-4-methylpiperazine (8.45 g.) dissolved in anhydrous dimethylformamide (50 cc.) is then added. After stirring for 2½ hours at 5° C., the reaction mixture is diluted with ice-water (500 cc.). The precipitate which has appeared is filtered off, washed four times with distilled water (total 200 cc.) and twice with diethyl ether (total 50 cc.) and then dissolved in methylene chloride (300 cc.). The organic solution is washed four times with distilled water (total 160 cc.), dried over anhydrous sodium sulphate, treated with decolourising charcoal (0.2 g.) and evaporated. When the residue liquid reaches a volume of 50 cc., boiling acetonitrile (200 cc.) is added. After cooling for 2 hours at 2° C., the crystals which have appeared are filtered off, washed three times with ice-cold acetonitrile (total 15 cc.) and dried under reduced pressure (20 mm. Hg). The crystals thus isolated (8.0 g.) are dissolved in boiling acetonitrile (270 cc.), decolourising charcoal (0.2 g.) is added to the boiling solution and the whole is filtered. After 24 hours at 2° C., the crystals which have appeared are filtered off, washed three times with ice-cold acetonitrile (total 10 cc.) and dried under reduced pressure (20 mm. Hg). 5-(4-Methylpiperazin-1-yl)carbonyloxy-6-(1,8-naphthyridin-2-yl)-7-oxo-2,3,6,7-tetrahydro-1,4-dithiino[2,3-c]pyrrole (5.8 g.), melting at 255° C., is thus obtained.

5-Hydroxy-6-(1,8-naphthyridin-2-yl)-7-oxo-2,3,6,7-tetrahydro-1,4-dithiino[2,3-c]pyrrole employed as starting material can be obtained in the following way:
Preparation of 2-amino-1,8-naphthyridine, m.p. 142° C., according to W. W. Paddler and Th. J. Kress, J. Org. Chem., 33, 1384 (1968).
Preparation of 5,7-dioxo-6-(1,8-naphthyridin-2-yl)-2,3,6,7-tetrahydro-1,4-dithiino[2,3-c]pyrrole (16.0 g.), m.p. 200° C., by reacting 2-amino-1,8-naphthyridine (8.65 g.) with 5,6-dihydro-1,4-dithiine-2,3-dicarboxylic acid anhydride (22.0 g.) [prepared according to the method of H. R. Schweizer, Helv. Chim. Acta, 52, 2229 (1969)] in diphenyl ether (70 cc.) at 150° C. for half an hour, in the presence of anhydrous acetic acid (0.4 cc.).
Preparation of 5-hydroxy-6-(1,8-naphthyridin-2-yl)-7-oxo-2,3,6,7-tetrahydro-1,4-dithiino[2,3-c]pyrrole (13.0 g.), m.p. 260° C., by reacting sodium borohydride (2.15 g.) with 5,7-dioxo-6-(1,8-naphthyridin-2-yl)-2,3,6,7-tetrahydro-1,4-dithiino[2,3-c]pyrrole (18.0 g.) in anhydrous tetrahydrofuran (200 cc.) to which anhydrous methanol (80 cc.) has been added gradually, at a temperature not exceeding 40° C.

EXAMPLE 17

6-(5-Chloro-1,8-naphthyridin-2-yl)-5-hydroxy-7-oxo-2,3,6,7-tetrahydro-1,4-dithiino[2,3-c]pyrrole (11.9 g.) is added, at 0° C., to a suspension of sodium hydride (1.2 g.) in anhydrous dimethylformamide (120 cc.). The reaction mixture is stirred for 1 hour at 5° C., and 1-chlorocarbonyl-4-methylpiperazine (16.6 g.) dissolved in anhydrous dimethylformamide (80 cc.) is then added. After stirring for 2½ hours at 5° C., the crystals which have appeared are filtered off and washed twice with diethyl ether (60 cc.). The product thus isolated is dissolved in an ice-cold 2N aqueous solution of methanesulphonic acid (200 cc.). The aqueous acid solution is washed with diethyl ether (80 cc.), and rendered alkaline by adding an excess of 10N sodium hydroxide solution. The oil which separates out is extracted twice with methylene chloride (total 400 cc.). The organic solution is washed three times with distilled water (total 240 cc.), dried over anhydrous sodium sulphate, treated with decolourising charcoal (0.2 g.) and evaporated. The crystals obtained (10.1 g.), m.p. 238° C., are dissolved in a boiling mixture of acetonitrile (200 cc.) and methylene chloride (180 cc.). After distilling off the methylene chloride and then cooling the residue for 1 hour at 2° C., the crystals which have appeared are filtered off, washed twice with ice-cold acetonitrile (total 40 cc.) and dried under reduced pressure (20 mm. Hg). 6-(5-Chloro-1,8-naphthyridin-2-yl)-5-(4-methylpiperazin-1-yl)carbonyloxy-7-oxo-2,3,6,7-tetrahydro-1,4-dithiino[2,3-c]pyrrole (8.0 g.), melting at 240° C., is thus obtained.

6-(5-Chloro-1,8-naphthyridin-2-yl)-5-hydroxy-7-oxo-2,3,6,7-tetrahydro-1,4-dithiino[2,3-c]pyrrole can be obtained in the following way:
Preparation of 2-amino-5-hydroxy-1,8-naphthyridine, m.p. 300°–305° C., according to S. Carboni et al., Gazz.

Chim. Ital., 101, 136 (1971).

Preparation of 5,7-dioxo-6-(5-hydroxy-1,8-naphthyridin-2-yl)-2,3,6,7-tetrahydro-1,4-dithiino[2,3-c]pyrrole (21.6 g.), m.p. 373° C., by reacting 2-amino-5-hydroxy-1,8-naphthyridine (13.8 g.) with 5,6-dihydro-1,4-dithiine-2,3-dicarboxylic acid anhydride (32.0 g.) in a mixture (250 cc.) of diphenyl and diphenyl ether (26.5–73.5 by weight) at 200° C. for 2 hours in the presence of anhydrous acetic acid (0.5 cc.).

Preparation of 6-(5-chloro-1,8-naphthyridin-2-yl)-5,7-dioxo-2,3,6,7-tetrahydro-1,4-dithiino[2,3-c]pyrrole (12.9 g.), m.p. 269° C., by reacting phosphorus pentachloride (10.0 g.) and phosphorus oxychloride (30.0 cc.) with 5,7-dioxo-6-(5-hydroxy-1,8-naphthyridin-2-yl)-2,3,6,7-tetrahydro-1,4-dithiino[2,3-c]pyrrole (13.6 g.) at about 100° C. for 1 hour.

Preparation of 6-(5-chloro-1,8-naphthyridin-2-yl)-5-hydroxy-7-oxo-2,3,6,7-tetrahydro-1,4-dithiino[2,3-c]pyrrole (10.6 g.), m.p. 266°–268° C., by reacting sodium borohydride (1.40 g.) with 6-(5-chloro-1,8-naphthyridin-2-yl)-5,7-dioxo-2,3,6,7-tetrahydro-1,4-dithiino[2,3-c]pyrrole (12.9 g.) in anhydrous tetrahydrofuran (120 cc.) to which anhydrous methanol (48 cc.) has been added gradually, at a temperature not exceeding 37° C.

EXAMPLE 18

Following the procedure of Example 17 but starting with 6-(7-chloro-1,8-naphthyridin-2-yl)-5-hydroxy-7-oxo-2,3,6,7-tetrahydro-1,4-dithiino[2,3-c]pyrrole (8.5 g.), sodium hydride (0.7 g.) and 1-chlorocarbonyl-4-methylpiperazine (11.9 g.) in anhydrous dimethylformamide (150 cc.), stirring the reaction mixture for 4 hours at 5° C. and then diluting it with ice-water (1,500 cc.), 6-(7-chloro-1,8-naphthyridin-2-yl)-5-(4-methylpiperazin-1-yl)carbonyloxy-7-oxo-2,3,6,7-tetrahydro-1,4-dithiino[2,3-c]pyrrole (0.76 g.), melting at 280° C. after recrystallisation from acetonitrile, is obtained.

6-(7-Chloro-1,8-naphthyridin-2-yl)-5-hydroxy-7-oxo-2,3,6,7-tetrahydro-1,4-dithiino[2,3-c]pyrrole employed as starting material can be obtained in the following way:

Preparation of 2-amino-7-hydroxy-1,8-naphthyridine, m.p. above 360° C., according to S. Carboni et al., Ann. di Chim. (Roma), 54, 883 (1964).

Preparation of 5,7-dioxo-6-(7-hydroxy-1,8-naphthyridin-2-yl)-2,3,6,7-tetrahydro-1,4-dithiino[2,3-c]pyrrole (13.0 g.), m.p. 342° C., by reacting 2-amino-7-hydroxy-1,8-naphthyridine (8.0 g.) with 5,6-dihydro-1,4-dithiine-2,3-dicarboxylic acid anhydride (18.8 g.) in a mixture (150 cc.) of diphenyl and diphenyl ether (26.5–73.5 by weight) at 230° C. for 2 hours, in the presence of anhydrous acetic acid (0.4 cc.).

Preparation of 6-(7-chloro-1,8-naphthyridin-2-yl)-5,7-dioxo-2,3,6,7-tetrahydro-1,4-dithiino[2,3-c]pyrrole (9.7 g.), m.p. 250° C., by reacting phosphorus oxychloride (45 cc.) with 5,7-dioxo-6-(7-hydroxy-1,8-naphthyridin-2-yl)-2,3,6,7-tetrahydro-1,4-dithiino[2,3-c]pyrrole (10.6 g.) at about 100° C. for 1 hour 45 minutes, in the presence of anhydrous dimethylformamide (1.9 cc.). Preparation of 6-(7-chloro-1,8-naphthyridin-2-yl)-5-hydroxy-7-oxo-2,3,6,7-tetrahydro-1,4-dithiino[2,3-c]pyrrole (1.4 g.), m.p. 315° C., by reacting potassium borohydride (0.4 g.) with 6-(7-chloro-1,8-naphthyridin-2-yl)-5,7-dioxo-2,3,6,7-tetrahydro-1,4-dithiino[2,3-c]pyrrole (1.7 g.) in anhydrous methanol (16 cc.) at a temperature of about 25°–30° C.

EXAMPLE 19

Following the procedure of Example 17 but starting with 6-(2-chloro-4-methyl-1,8-naphthyridin-7-yl)-5-hydroxy-7-oxo-2,3,6,7-tetrahydro-1,4-dithiino[2,3-c]pyrrole (16.7 g.), sodium hydride (1.65 g.) and 1-chlorocarbonyl-4-methylpiperazine (22.0 g.) in anhydrous dimethylformamide (280 cc.) stirring the reaction mixture for 4 hours at 5° C. and then diluting it with ice-water (2,800 cc.), 6-(2-chloro-4-methyl-1,8-naphthyridin-7-vl)-5-(4-methylpiperazin-1-yl)carbonyloxy-7-oxo-2,3,6,7-tetrahydro-1,4-dithiino[2,3-c]pyrrole (11.7 g.), melting at 233° C. after recrystallisation from acetonitrile, is obtained.

6-(2-Chloro-4-methyl-1,8-naphthyridin-7-yl)-5-hydroxy-7-oxo-2,3,6,7-tetrahydro-1,4-dithiino[2,3-c]pyrrole employed as starting material can be obtained in the following way:

Preparation of 7-amino-2-hydroxy-4-methyl-1,8-naphthyridine, m.p. above 400° C., according to O. Seide, Chem. Ber., 59, 2465 (1926).

Preparation of 5,7-dioxo-6-(2-hydroxy-4-methyl-1,8-naphthyridin-7-yl)-2,3,6,7-tetrahydro-1,4-dithiino[2,3-c]pyrrole (14.3 g.), m.p. 305° C., by reacting 7-amino-2-hydroxy-4-methyl-1,8-naphthyridine (10.0 g.) with 5,6-dihydro-1,4-dithiine-2,3-dicarboxylic acid anhydride (21.4 g.) in a mixture (170 cc.) of diphenyl and diphenyl ether (26.5–73.5 by weight) at 230° C. for 4 hours, in the presence of anhydrous acetic acid (0.4 cc.). Preparation of 6-(2-chloro-4-methyl-1,8-naphthyridin-7-yl)-5,7-dioxo-2,3,6,7-tetrahydro-1,4-dithiino[2,3-c]pyrrole (36.6 g.), m.p. 280° C, by reacting phosphorus pentachloride (23.5 g.) and phosphorus oxychloride (70 cc.) with 6-(2-hydroxy-4-methyl-1,8-naphthyridin-7-yl)-2,3,6,7-tetrahydro-1,4-dithiino[2,3-c]pyrrole (35.2 g.) at about 100° C. for 2 hours.

Preparation of 6-(2-chloro-4-methyl-1,8-naphthyridin-7-yl)-5-hydroxy-7-oxo-2,3,6,7-tetrahydro-1,4-dithiino[2,3-c]pyrrole (16.8 g.), m.p. 300° C, by reacting sodium borohydride (2.1 g.) with 6-(2-chloro-4-methyl-1,8-naphthyridin-7-yl)-5,7-dioxo-2,3,6,7-tetrahydro-1,4-dithiino[2,3-c]pyrrole (20.0 g.) in anhydrous tetrahydrofuran (200 cc.) to which anhydrous methanol (80 cc.) has been added gradually, at a temperature of about 30° C.

EXAMPLE 20

Following the procedure of Example 17 but starting with 5-hydroxy-6-(7-methoxy-1,8-naphthyridin-2-yl)-7-oxo-2,3,6,7-tetrahydro-1,4-dithiino[2,3-c]pyrrole (5.25 g.), sodium hydride (0.45 g.) and 1-chlorocarbonyl-4-methylpiperazine (4.85 g.) in anhydrous dimethylformamide (100 cc.), stirring the reaction mixture for 3 hours at 5° C, and then diluting it with ice-water (500 cc.), 6-(7-methoxy-1,8-naphthyridin-2-yl)-5-(4-methylpiperazin-1-yl)carbonyloxy-7-oxo-2,3,6,7-tetrahydro-1,4-dithiino[2,3-c]pyrrole (5.0 g.), melting at 240° C, after recrystallisation from acetonitrile, is obtained.

5-Hydroxy-6-(7-methoxy-1,8-naphthyridin-2-yl)-7-oxo-2,3,6,7-tetrahydro-1,4-dithiino[2,3-c]pyrrole employed as starting material can be obtained in the following way:

Preparation of 2-acetylamino-7-chloro-1,8-naphthyridine, m.p. 251°–253° C, according to S. Carboni et al, Gazz. Chim. Ital., 95, 1492 (1965).

Preparation of 2-amino-7-methoxy-1,8-naphthyridine (1.0 g.), m.p. 156° C, by reacting sodium methoxide (1.8 g.) with 2-acetylamino-7-chloro-1,8-naphthyridine (2.2 g.) in refluxing anhydrous methanol (40 cc.) for 1 hour.

Preparation of 5,7-dioxo-6-(7-methoxy-1,8-naphthyridin-2-yl)-2,3,6,7-tetrahydro-1,4-dithiino[2,3-c]pyrrole (18.9 g.), m.p. 295° C, by reacting 2-amino-7-methoxy-1,8-naphthyridine (11.4 g.) with 5,6-dihydro-1,4-dithiine-2,3-dicarboxylic acid anhydride (24.5 g.) in diphenyl ether (70 cc.) at 140° C. for half an hour, in the presence of anhydrous acetic acid (0.4 cc.).

Preparation of 5-hydroxy-6-(7-methoxy-1,8-naphthyridin-2-yl)-7-oxo-2,3,6,7-tetrahydro-1,4-dithiino[2,3-c]pyrrole (15.1 g.), m.p. 255°C, by reacting sodium borohydride (2.1 g.) with 5,7-dioxo-6-(7-methoxy-1,8-naphthyridin-2-yl)-2,3,6,7-tetrahydro-1,4-dithiino[2,3-c]pyrrole (18.9 g.) in anhydrous tetrahydrofuran (200 cc.) to which anhydrous methanol (80 cc.) has been added gradually, at a temperature not exceeding 40°C.

EXAMPLE 21

Following the procedure of Example 16 but starting with 5-hydroxy-6-(7-methyl-1,8-naphthyridin-2-yl)-7-oxo-2,3,6,7-tetrahydro-1,4-dithiino[2,3-c]pyrrole (5.9 g.), sodium hydride (1.40 g.) and 1-chlorocarbonyl-4-methylpiperazine (11.5 g.) in anhydrous dimethylformamide (77 cc.) and stirring the reaction mixture for 4 hours at 5°C, 6-(7-methyl-1,8-naphthyridin-2-yl)-5-(4-methylpiperazine-1-yl)carbonyloxy-7-oxo-2,3,6,7-tetrahydro-1,4-dithiino[2,3-c]pyrrole (2.2 g.), melting at 233°C. after recrystallisation from ethanol, is obtained.

5-Hydroxy-6-(7-methyl-1,8-naphthyridin-2-yl)-7-oxo-2,3,6,7-tetrahydro-1,4-dithiino[2,3-c]pyrrole employed as starting material can be obtained in the following way:

Preparation of 2-amino-7-methyl-1,8-naphthyridine, m.p. 186°–187°, according to E. U. Brown, J. Org. Chem., 30, 1607 (1965).

Preparation of 6-(7-methyl-1,8-naphthyridin-2-yl)-5,7-dioxo-2,3,6,7-tetrahydro-1,4-dithiino[2,3-c]pyrrole (14.5 g.), m.p. 285°C, by reacting 2-amino-7-methyl-1,8-naphthyridine (12.0 g.) with 5,6-dihydro-1,4-dithiine-2,3-dicarboxylic acid anhydride (17.4 g.) in diphenyl ether (75 cc.) at 140°C. for 3½ hours, in the presence of anhydrous acetic acid (1.5 cc.). Preparation of 5-hydroxy-6-(7-methyl-1,8-naphthyridin-2-yl)-7-oxo-2,3,6,7-tetrahydro-1,4-dithiino[2,3-c]pyrrole (10.1 g.), m.p. 275°C, by reacting sodium borohydride (1.7 g.) with 6-(7-methyl-1,8-naphthyridin-2-yl)-5,7-dioxo-2,3,6,7-tetrahydro-1,4-dithiino[2,3-c]pyrrole (14.5 g.) in anhydrous tetrahydrofuran (150 cc.) to which anhydrous methanol (60 cc.) has been added gradually, at a temperature not exceeding 44°C.

EXAMPLE 22

Following the procedure of Example 17 but starting with 5-hydroxy-6-(5-methyl-1,8-naphthyridin-2-yl)-7-oxo-2,3,6,7-tetrahydro-1,4-dithiino[2,3-c]pyrrole (11.8 g.), sodium hydride (1.1 g.) and 1-chlorocarbonyl-4-methylpiperazine (11.6 g.) in anhydrous dimethylformamide (250 cc.), stirring the reaction mixture for 4 hours at 5°C. and then diluting it with ice-water (750 cc.), 6-(5-methyl-1,8-naphthyridin-2-yl)-5-(4-methylpiperazin-1-yl)carbonyloxy-7-oxo-2,3,6,7-tetrahydro-1,4-dithiino-[2,3-c]pyrrole (4.5 g.), melting at 200°C. after recrystallisation from ethanol, is obtained.

5-Hydroxy-6-(5-methyl-1,8-naphthyridin-2-yl)-7-oxo-2,3,6,7-tetrahydro-1,4-dithiino[2,3-c]pyrrole employed as starting material can be obtained in the following way:

Preparation of 2-amino-5-methyl-1,8-naphthyridine, m.p. 207°C, according to E. U. Brown, J. Org. Chem., 30, 1609 (1965).

Preparation of 6-(5-methyl-1,8-naphthyridin-2-yl)-5,7-dioxo-2,3,6,7-tetrahydro-1,4-dithiino[2,3-c]pyrrole (15.1 g.), m.p. 275°C, by reacting 2-amino-5-methyl-1,8-naphthyridine (9.6 g.) with 5,6-dihydro-1,4-dithiine-2,3-dicarboxylic acid anhydride (22.8 g.) in diphenyl ether (50 cc.) at 140°C. for 3 hours in the presence of anhydrous acetic acid (0.5 cc.).

Preparation of 5-hydroxy-6-(5-methyl-1,8-naphthyridin-2-yl)-7-oxo-2,3,6,7-tetrahydro-1,4-dithiino[2,3-c]pyrrole (11.0 g.), m.p. 280°C, by reacting sodium borohydride (1.85 g.) with 6-(5-methyl-1,8-naphthyridin-2-yl)-5,7-dioxo-2,3,6,7-tetrahydro-1,4-dithiino[2,3-c]pyrrole (16.0 g.) in anhydrous tetrahydrofuran (200 cc.) to which anhydrous methanol (80 cc.) has been added gradually, at a temperature not exceeding 40°C.

EXAMPLE 23

Following the procedure of Example 16 but starting with 5-hydroxy-6-(2,4-dimethyl-1,8-naphthyridin-7-yl)-7-oxo-2,3,6,7-tetrahydro-1,4-dithiino[2,3-c]pyrrole (15.0 g.), sodium hydride (1.15 g.) and 1-chlorocarbonyl-4-methylpiperazine (13.8 g.) in anhydrous dimethylformamide (250 cc.) and stirring the reaction mixture for 4 hours at 5°C, 6-(2,4-dimethyl-1,8-naphthyridin-7-yl)-5-(4-methylpiperazin-1-yl)carbonyloxy-7-oxo-2,3,6,7-tetrahydro-1,4-dithiino[2,3-c]pyrrole (1.9 g.), melting at 223°–224°C. after recrystallisation from ethanol, is obtained.

5-Hydroxy-6-(2,4-dimethyl-1,8-naphthyridin-7-yl)-7-oxo-2,3,6,7-tetrahydro-1,4-dithiino[2,3-c]pyrrole employed as starting material can be obtained in the following way:

Preparation of 7-amino-2,4-dimethyl-1,8-naphthyridine, m.p. 225°–226°C, according to J. Bernstein et al., J. Amer. Chem. Soc., 69, 1151 (1947).

Preparation of 6-(2,4-dimethyl-1,8-naphthyridin-7-yl)-5,7-dioxo-2,3,6,7-tetrahydro-1,4-dithiino[2,3-c]pyrrole (25.0 g.), m.p. 275°–280°C, by reacting 7-amino-2,4-dimethyl-1,8-naphthyridine (17.3 g.) with 5,6-dihydro-1,4-dithiine-2,3-dicarboxylic acid anhydride (22.5 g.) in diphenyl ether (100 cc.) at 170°C. for 1 hour, in the presence of anhydrous acetic acid (2.0 cc.).

Preparation of 5-hydroxy-6-(2,4-dimethyl-1,8-naphthyridin-7-yl)-7-oxo-2,3,6,7-tetrahydro-1,4-dithiino[2,3-c]pyrrole (21.5 g.), m.p. 330°C, by reacting sodium borohydride (2.7 g.) with 6-(2,4-dimethyl-1,8-naphthyridin-7-yl)-5,7-dioxo-2,3,6,7-tetrahydro-1,4-dithiino[2,3-c]pyrrole (24.0 g.) in anhydrous tetrahydrofuran (250 cc.) to which anhydrous methanol (100 cc.) has been added gradually, at a temperature not exceeding 50°C.

EXAMPLE 24

Following the procedure of Example 17 but starting with 5-hydroxy-6-(5-methoxy-1,8-naphthyridin-2-yl)-7-oxo-2,3,6,7-tetrahydro-1,4-dithiino[2,3-c]pyrrole (1.05 g.), sodium hydride (0.09 g.) and 1-chlorocarbonyl-4-methylpiperazine (1.0 g.) in anhydrous dimethylformamide (25 cc.), stirring the reaction mixture for 4 hours at 5°C. and then diluting it with ice-water (200 cc.), 6-(5-methoxy-1,8-naphthyridin-2-yl)-5-(4-methylpiperazin-1-yl)carbonyloxy-7-oxo-2,3,6,7-tetrahydro-1,4-dithiino[2,3-c]pyrrole (0.23 g.), melting at 268°C. after crystallisation from acetonitrile, is obtained.

5-Hydroxy-6-(5-methoxy-1,8-naphthyridin-2-yl)-7-oxo-2,3,6,7-tetrahydro-1,4-dithiino[2,3-c]pyrrole employed as starting material can be obtained in the following way:

Preparation of 2-acetylamino-5-chloro-1,8-naphthyridine, m.p. 265°C, according to S. Carboni et al., Gazz. Chim. Ital., 101, 137 (1971).

Preparation of 2-amino-5-methoxy-1,8-naphthyridine (7.5 g.), m.p. 240°C, by reacting sodium methoxide (10.8 g.) with 2-acetylamino-5-chloro-1,8-naphthyridine (11.0 g.) in refluxing anhydrous methanol (100 cc.) for 6 hours.

Preparation of 6-(5-methoxy-1,8-naphthyridin-2-yl)-5,7-dioxo-2,3,6,7-tetrahydro-1,4-dithiino[2,3-c]pyrrole (8.8 g.), m.p. 315°C, by reacting 2-amino-5-methoxy-1,8-naphthyridine (7.35 g.) with 5,6-dihydro-1,4-dithiine-2,3-dicarboxylic acid anhydride (16.0 g.) in diphenyl ether (75 cc.) at 150°C. for 2 hours, in the presence of anhydrous acetic acid (0.3 cc.).

Preparation of 5-hydroxy-6-(5-methoxy-1,8-naphthyridin-2-yl)-7-oxo-2,3,6,7-tetrahydro-1,4-dithiino[2,3-c]pyrrole (8.3 g.), m.p. 315°C, by reacting sodium borohydride (1.0 g.) with 6-(5-methoxy-1,8-naphthyridin-2-yl)-5,7-dioxo-2,3,6,7-tetrahydro-1,4-dithiino[2,3-c]pyrrole (9.0 g.) in anhydrous tetrahydrofuran (80 cc.) to which anhydrous methanol (32 cc.) has been added gradually, at a temperature of about 25°–30°C.

EXAMPLE 25

A 3.16N solution of sodium methoxide in methanol (6.7 cc.) is added to a suspension of 1-methylpiperazine-1-oxide dihydrochloride (2.0 g.) in anhydrous methanol (10 cc.). After stirring for 10 minutes at 25°C, the suspension is treated with decolourising charcoal (0.1 g.) and the suspension filtered. The methanolic filtrate is evaporated under reduced pressure (20 mm. Hg) at a maximum temperature of 40°C. The oily residue (2.0 g.) is dissolved in anhydrous acetonitrile (20 cc.) and 6-(5-chloropyrid-2-yl)-7-oxo-5-phenoxycarbonyloxy-2,3,6,7-tetrahydro-1,4-dithiino[2,3-c]pyrrole (2.1 g.) is added. The reaction mixture is stirred for 48 hours at a temperature of about 25°C, and is then filtered and evaporated under reduced pressure (20 mm. Hg). The oily residue (4.2 g.) is dissolved in anhydrous ethanol (20 cc.) and a 4.5N solution of anhydrous hydrogen chloride in diethyl ether (3.34 cc.) is added. After cooling for 2 hours at 2°C, the crystals which have appeared are filtered off, washed with ice-cold anhydrous ethanol (3 cc.), then with distilled water (10 cc.) and twice with diethyl ether (total 20 cc.), and dried under reduced pressure (20 mm. Hg). 4-[6-(5-Chloropyrid-2-yl)-7-oxo-2,3,6,7-tetrahydro-1,4-dithiino[2,3-c]pyrrol-5-yl]-oxycarbonyl-1-methylpiperazine-1-oxide hydrochloride (1.0 g.), melting at 231°C, is obtained.

1-Methylpiperazine-1-oxide dihydrochloride employed as starting material can be obtained in the following way:

Preparation of (oily) t-butyl (4-methylpiperazin-1-yl)-carboxylate (15.0 g.) by reacting t-butyl azidoformate (12.9 g.) with 1-methylpiperazine (9.5 g.) in water (30 cc.) and tetrahydrofuran (15 cc.), whilst gradually adding a 5N sodium hydroxide solution (19 cc.), at a temperature of about 20°C.

Preparation of 1-methyl-4-(t-butoxycarbonyl)piperazine-1-oxide hydrochloride (8.7 g.), m.p. 233°C, by reacting 4-nitroperbenzoic acid (34.0 g.) with t-butyl (4-methylpiperazin-1-yl)-carboxylate (24.2 g.) in anhydrous chloroform (240 cc.) at a temperature not exceeding 40°C.

Preparation of 1-methylpiperazine-1-oxide dihydrochloride (5.5 g.), m.p. 205°C, by reacting anhydrous hydrogen chloride gas (2.35 g.) with 1-methyl-4-(t-butoxycarbonyl)-piperazine-1-oxide hydrochloride (8.1 g.) in refluxing anhydrous ethanol (60 cc.) for half an hour.

EXAMPLE 26

1-Methylpiperazine (1.25 g.) is added to a suspension of 6-(2-methoxy-4-methyl-1,8-naphthyridin-7-yl)-7-oxo-5-phenoxycarbonyloxy-2,3,6,7-tetrahydro-1,4-dithiino[2,3-c]pyrrole (2.00 g.) in anhydrous acetonitrile (30 cc.). The reaction mixture is stirred for 21 hours at a temperature of about 20°C. 1-Methylpiperazine (3.8 g.) is added and the reaction mixture is heated for 4 hours at a temperature of about 45°C. After cooling, the reaction mixture is treated with decolourising charcoal (0.2 g.). After filtering and evaporating the solvent, the residue is dissolved in methylene chloride (50 cc.). The organic solution is washed twice with N sodium hydroxide solution (total 100 cc.) and twice with distilled water (total 100 cc.), treated with decolourising charcoal (0.1 g.) and evaporated. The residue is treated with a 0.5N aqueous solution of methanesulphonic acid (40 cc.). After filtration, the aqueous acid solution is rendered alkaline by adding 5N sodium hydroxide solution (10 cc.). The oil which separates out is extracted twice with methylene chloride (total 100 cc.). The organic solution is washed twice with distilled water (total 80 cc.), dried over anhydrous sodium sulphate and evaporated. The residue (1.85 g.) is dissolved in boiling ethanol (12 cc.). After cooling the ethanolic solution for 2 hours at 2°C, the crystals which have appeared are filtered off, washed twice with ice-cold ethanol (total 4 cc.) and dried under reduced pressure (20 mm. Hg). 6-(2-Methoxy-4-methyl-1,8-naphthyridin-7-yl)-5-(4-methylpiperazin-1-yl)carbonyloxy-7-oxo-2,3,6,7-tetrahydro-1,4-dithiino[2,3-c]pyrrole (0.9 g.), which melts at 232°–234°C, is obtained.

6-(2-Methoxy-4-methyl-1,8-naphthyridin-7-yl)-7-oxo-5-phenoxycarbonyloxy-2,3,6,7-tetrahydro-1,4-dithiino[2,3-c]pyrrole employed as starting material can be obtained in the following way:

Preparation of 7-acetylamino-2-chloro-4-methyl-1,8-naphthyridine, m.p. 242°–243°C, according to J. Petrow, J. Chem. Soc., 1407 (1947).

Preparation of 7-amino-2-methoxy-4-methyl-1,8-naphthyridine (78.0 g.), m.p. 240°C, by reacting sodium methoxide (81.0 g.) with 7-acetylamino-2-chloro-4-methyl-1,8-naphthyridine (117.5 g.) in refluxing anhydrous methanol (600 cc.) for 8 hours.

Preparation of 6-(2-methoxy-4-methyl-1,8-naphthyridin-7-yl)-5,7-dioxo-2,3,6,7-tetrahydro-1,4-dithiino[2,3-c]pyrrole (20.0 g.), m.p. about 380°C, by reacting 7-amino-2-methoxy-4-methyl-1,8-naphthyridine (13.3 g.) with 5,6-dihydro-1,4-dithiine-2,3-dicarboxylic acid anhydride (26.6 g.) in diphenyl ether (105 cc.) at 230°–240°C, for 3 hours, in the presence of anhydrous acetic acid (0.5 cc.).

Preparation of 5-hydroxy-6-(2-methoxy-4-methyl-1,8-naphthridin-7-yl)-7-oxo-2,3,6,7-tetrahydro-1,4-dithiino[2,3-c]pyrrole (12.0 g.) m.p. about 390°C, by reacting sodium borohydride (4.8 g.) with 6-(2-methoxy-4-methyl-1,8-naphthyridin-7-yl)-5,7-dioxo-2,3,6,7-tetrahydro-1,4-dithiino[2,3-c]pyrrole (22.7 g.) in anhydrous tetrahydrofuran (250 cc.) to which anhydrous methanol (100 cc.) has been added gradually at a temperature not exceeding 30°C.

Preparation of 6-(2-methoxy-4-methyl-1,8-naphthyridin-7-yl)-7-oxo-5-phenoxycarbonyloxy-2,3,6,7-tetrahydro-1,4-dithiino[2,3-c]pyrrole (2.1 g.), m.p. 250°C, by reacting phenyl chloroformate (2.35 g.) with 5-hydroxy-6-(2-methoxy-4-methyl-1,8-naphthyridin-7-yl)-7-oxo-2,3,6,7-tetrahydro-1,4-dithiino[2,3-c]pyrrole (1.8 g.) in anhydrous pyridine (20 cc.) at a temperature not exceeding 40°C.

The present invention includes within its scope pharmaceutical compositions comprising, as active ingredient, at least one of the compounds of general formula I, or a non-toxic acid addition salt thereof, in association with a pharmaceutical carrier or coating. The invention includes especially such preparations made up for oral, parenteral or rectal administration or as ointments.

Solid compositions for oral administration include tablets, pills, powders and granules. In such solid compositions the active compound is admixed with at least one inert diluent such as sucrose, lactose or starch. The compositions may also comprise, as is normal practice, additional substances other than inert diluents, e.g. lubricating agents, such as magnesium stearate. Liquid compositions for oral administration include pharmaceutically-acceptable emulsions, solutions, suspensions, syrups and elixirs containing inert diluents commonly used in the art, such as water or liquid paraffin. Besides inert diluents such compositions may also comprise adjuvants, such as wetting, emulsifying and suspending agents, and sweetening, flavouring and aromatizing agents. The compositions according to the invention, for oral administration, also include capsules of absorbable material such as gelatin containing the active substance with or without the addition or diluents or excipients.

Preparations according to the invention for parenteral administration include sterile aqueous or non-aqueous solutions, suspensions or emulsions. Examples of non-aqueous solvents or vehicles are propylene glycol, polyethylene glycol, vegetable oils such as olive oil, and injectable organic esters such as ethyl oleate. These compositions may also contain adjuvants such as preserving, wetting, emulsifying and dispersing agents. They may be sterilized by, for example, filtration through a bacteria-retaining filter, by incorporation in the compositions of sterilizing agents, by irradiation, or by heating. They may also be manufactured in the form of sterile solid compositions, which can be dissolved in sterile water or some other sterile injectable medium immediately before use.

Compositions for rectal administration are suppositories which contain, in addition to the active substance, excipients such as cacao butter or a suitable wax base.

The percentage of active ingredient in the compositions of the invention may be varied, it being necessary that it should constitute a proportion such that a suitable dosage shall be obtained. The dosage depends on the desired therapeutic effect, on the route of administration and on the duration of the treatment. The compositions are particularly useful in human therapy because of their tranquillising effects, their anti-convulsant effect, their effect in overcoming contractures and their effect in producing hypnosis. In human therapy the compositions when administered orally to and adult should generally give doses between 20 mg. and 500 mg. of active substance per day. In general the physician will decide the posology considered appropriate, taking into account the age and weight and other factors intrinsic to the patient being treated.

The following Examples illustrate pharmaceutical compositions according to the invention.

EXAMPLE 27

Tablets containing 25 mg. of active product and having the following composition are prepared in accordance with the usual technique:

| | |
|---|---|
| 6-(5-chloropyrid-2-yl)-5-(4-methyl-piperazin-1-yl)carbonyloxy-7-oxo-2,3,6,7-tetrahydro-1,4-dithiino[2,3-c]pyrrole | 0.025 g. |
| starch | 0.090 g. |
| precipitated silica | 0.030 g. |
| magnesium stearate | 0.005 g. |

EXAMPLE 28

Tablets containing 25 mg. of active product and having the following composition are prepared in accordance with the usual technique:

| | |
|---|---|
| 6-(7-chloro-1,8-naphthyridin-2-yl)-5-(4-methylpiperazin-1-yl)carbonyloxy-7-oxo-2,3,6,7-tetrahydro-1,4-dithiino-[2,3-c]pyrrole | 0.025 g. |
| starch | 0.090 g. |
| precipitated silica | 0.030 g. |
| magnesium stearate | 0.005 g. |

We claim:

1. A 1,4-dithiino[2,3-c]pyrrole of the formula:

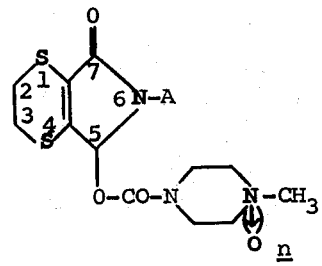

wherein A is phenyl, 2-pyridyl, 3-pyridazinyl, 2-quinolyl or 1,8-naphthyridin-2-yl, or a said radical singly substituted by halogen, alkyl of 1 through 4 carbon atoms, alkoxy of 1 through 4 carbon atoms, cyano or nitro, and $n$ is zero or 1, or a non-toxic pharmaceutically-acceptable acid addition salt thereof.

2. A 1,4-dithiino[2,3-c]pyrrole derivative according to claim 1, wherein $n$ is zero, or a non-toxic pharmaceutically-acceptable acid addition salt thereof.

3. A 1,4-dithiino[2,3-c]pyrrole derivative according to claim 1 wherein said halogen atom is chlorine, said alkyl radical is methyl, or said alkoxy radical is methoxy, or a non-toxic pharmaceutically-acceptable acid addition salt thereof.

4. 6-(7-Chloro-1,8-naphthyridin-2-yl)-5-(4-methylpiperazin-1-yl)carbonyloxy-7-oxo-2,3,6,7-tetrahydro- 1,4-dithiino[2,3-c]pyrrole or a non-toxic pharmaceutically-acceptable acid addition salt thereof.

5. 6-(7-Chloroquinol-2-yl)-5-(4-methylpiperazin-1-yl)carbonyloxy-7-oxo-2,3,6,7-tetrahydro-1,4-dithiino[2,3-c]pyrrole or a non-toxic pharmaceutically-acceptable acid addition salt thereof.

6. 6-(5-Chloropyrid-2-yl)-5-(4-methylpiperazin-1-yl)carbonyloxy-7-oxo-2,3,6,7-tetrahydro-1,4-dithiino[2,3-c]pyrrole or a non-toxic pharmaceutically-acceptable acid addition salt thereof.

7. 5-(4-Methylpiperazin-1-yl)carbonyloxy-6-(3-nitrophenyl)-7-oxo-2,3,6,7-tetrahydro-1,4-dithiino[2,3-c]pyrrole or a non-toxic pharmaceutically-acceptable acid addition salt thereof.

8. 5-(4-Methylpiperazin-1-yl)-carbonyloxy-6-(5-methylpyrid-2-yl)-7-oxo-2,3,6,7-tetrahydro-1,4-dithiino[2,3-c]pyrrole or a non-toxic pharmaceutically-acceptable acid addition salt thereof.

* * * * *